United States Patent [19]

Johnson

[11] 4,064,248

[45] * Dec. 20, 1977

[54] DOSAGE REGIMEN

[75] Inventor: Herbert G. Johnson, Kalamazoo, Mich.

[73] Assignee: The Upjohn Company, Kalamazoo, Mich.

[*] Notice: The portion of the term of this patent subsequent to Feb. 18, 1992, has been disclaimed.

[21] Appl. No.: 439,434

[22] Filed: Feb. 4, 1974

Related U.S. Application Data

[63] Continuation-in-part of Ser. No. 278,292, Aug. 7, 1972, abandoned.

[51] Int. Cl.$^2$ ............................................. A61K 31/47
[52] U.S. Cl. ................................................... 424/258
[58] Field of Search ..................... 424/258; 260/288 P

[56] References Cited

U.S. PATENT DOCUMENTS 3,563,981  2/1971  Lesher .................................. 260/287

OTHER PUBLICATIONS

Snyder et al. J.A.C.S. vol. 18, pp. 1320–1322.

Primary Examiner—Stanley J. Friedman
Attorney, Agent, or Firm—John J. Killinger; Roman Saliwanchik

[57] ABSTRACT

An improved dosage regimen for the administration of the pharmacologically acceptable salts or esters of a compound of the formula:

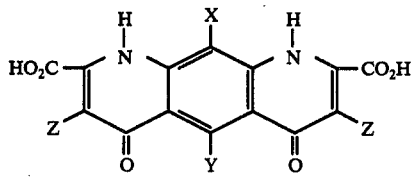

wherein X and Y can be the same or different and are selected from the group consisting of hydrogen, alkyl of from one to six carbon atoms, inclusive, cycloalkyl of five or six carbon atoms, inclusive, phenyl, hydroxyl, alkoxy having from one to three carbon atoms, inclusive, halogen, trifluoromethyl, cyano, carboxyamide and —CO$_2$H; Z is selected from the group consisting of hydrogen, alkyl from one to three carbon atoms, inclusive, and phenyl and provided when X is chloro at least one of Y and Z are other than hydrogen consisting of the initial administration of a priming dose (high) and thereafter administering a maintenance (low) dose of from 1/5th to 1/1000th of the priming dose, the maintenance doses being continually administered every 4 to 12 hours or as needed. The priming dose is re-administered followed by the maintenance doses whenever a 48 hour period without dosage administration occurs.

4 Claims, No Drawings

DOSAGE REGIMEN

CROSS REFERENCE TO RELATED APPLICATION

This application is a continuation-in-part of copending application Serial No. 278,292, filed August 7, 1972, now abandoned.

BRIEF SUMMARY OF THE INVENTION

This invention relates an improved dosage regimen for the administration of pharmacologically acceptable salts or esters of compounds of the formula I which provides an increased prophylactic effectiveness of the drug.

DETAILED DESCRIPTION OF THE INVENTION

The salts or esters of a compound of the formula I are effective in the prophlactic treatment of allergies of a reagin or non-reagin mediated nature. Primarily the compounds are used by oral inhalation for the treatment of asthma. The usual dosage regimen has been the administration of a single dosage amount with subsequent doses in the same dosage amount repeated every 4 to 12 hours. In the case of the antiasthmatic drug, cromolyn sodium (INTAL), this dosage schedule however, has been observed to result in a decrease in the prophylactic effect of the drug. That is to say, asthmatics upon repeating the usual dosage schedule have lost the prophylactic protection to the allergy, i.e., they become refractory to treatment.

The present invention overcomes the aforementioned problem encountered by the usual dosage schedule by reducing the second and continuing doses (i.e., maintenance doses) to 1/5th to 1/1000th (1/50th being preferred) of the usual initial dose.

After the initial or priming dose is administered, the smaller maintenance dose is given every 4 to 12 hours, e.g., 3 times a day during waking hours is preferred, as advised by the attending physician.

If a 48 hour period passes without the administration of the maintenance dose, the dosage regimen is started over commencing with a primary dose followed by maintenance doses. In some cases, the priming dose can be repeated one or more times, as advised by the physician, before the lower maintenance doses are instituted.

The salts or esters of a compound of the formula I are known and can be prepared by means disclosed in U.S. Patent application Ser. No. 230,034, filed Feb. 28, 1972, now abandoned.

The esters of the compounds of the formula I that are contemplated are the methyl, ethyl, propyl, isopropyl, and phenyl esters. The pharmacologically acceptable salts are the salts formed with a base providing a pharmacologically acceptable cation.

The compositions of a salt or ester of a compound of the formula I of the present invention are presented for administration to humans and animals in unit dosage forms, such as tablets, capsules, pills, powders, granules, sterile parenteral solutions or suspensions, and oral solutions or suspensions, and oil-in-water and water-in-oil emulsions containing suitable quantities of the active compound. The preferred method of administration is by inhalation into the lung by means of an aerosol or powder for insufflation.

For oral administration either solid or fluid unit dosage forms can be prepared. For preparing solid compositions such as tablets, the active compound is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydro-alcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The preferred compositions are those adapted for inhalation into the lung and containing a water soluble salt of a compound of the formula I.

Compositions for inhalation are of these basic types: (1) a powder mixture preferably micro-pulverized; (2) an aqueous solution or suspension to be sprayed with a nebulizer; and (3) an aerosol with volatile propellant in a pressurized container.

The powders are prepared quite simply by mixing a compound of the formula with a solid base which is compatible with lung tissue, preferably lactose. The powders are packaged in a device adapted to emit a measured amount of powder when inhaled through the mouth.

Aqueous solutions are prepared by dissolving a salt of the compound of the formula I in water and adding salt to provide an isotonic solution and buffering to a pH compatible with inhalation. Aqueous suspensions are prepared by suspending finely divided, preferably micro-pulverized, powders in an aqueous menstruum. A wetting agent may be added to facilitate dispersion. The solutions or suspensions are dispersed in a spray device or nebulizer and sprayed into the mouth while inhaling.

Aerosols are prepared by dissolving a salt or ester of a compound of the formula I in water or ethanol and mixing with a volatile propellant and placing in a pressurized container having a metering device to release a predetermined amount of material. The liquefied propellant employed is one which has a boiling point below 65° F. at atmospheric pressure. For use in compositions intended to produce aerosols for medicinal use, the liquefied propellant should be non-toxic. Among the suitable liquefied propellants which may be employed are the lower alkanes containing up to five carbon atoms, such as butane and pentane, or a lower alkyl chloride, such as methyl, ethyl, or propyl chlorides. The most suitable liquefied propellants are the fluorinated and fluorochlorinated lower alkanes such as are sold under the trademarks "Freon" and "Genetron". Mixtures of the above-mentioned propellants may suitably be employed. Examples of these propellants are dichlorodifluoromenthane ("Freon 12"), and dichlorotetrafluoroethane ("Freon 114").

The priming dose for the preferred compound, di(trishydroxymethyl)methylammonium 10-methyl-1,4,6,9-tetrahydro-4,6-dioxopyrido[3,2-g]quinoline-2,8-dicarboxylate is 1 mg. by oral inhalation. The maintenance dose is then given every 4 to 12 hours. It is from 0.001 mg. (1/1000) to 0.2 mg. (1/5) with 0.02 mg. (1/50) being preferred. The priming dose (high) of other compounds of formula I is an amount adequately to mitigate and control the allergic condition in the opinion of the attending physician. One criterion that can be used in the comparative anti-allergic activity of the compound to the activity of cromolyn, as judged, for example from the forced exhalation volume test (FEV.), the passive cutaneous anaphylaxis test, or other tests appropriate in the art. The maintenance dose is a subsequently administered and a reduced dose, being of the range of about 1/20th to 1/1000th of the priming dose, sufficient to maintain the anti-allergic condition, under the advice of the attending physician.

The administration of the compositions according to the dosage regimen of the present invention to humans and animals provides a method for the prophylactic treatment of allergy or anaphylactic reactions of a reagin or non-reagin mediated nature without the development or with the delayed development of a refractory state. That is to say, these compositions when administered according to the dosage regimen to a sensitized individual prior to the time that the individual comes into contact with substances (antigens), to which he is allergic, will prevent the allergic reaction which would otherwise occur and will maintain the protected state.

For example, the process can be used for prophylactic treatment of such chronic conditions as bronchial asthma, allergic rhinitis, food allergy, hay fever, urticaria, and autoimmune diseases.

EXAMPLE 1

PRIMING DOSE

A lot of 10,000 tablets, each containing 1 mg. of disodium 10-methyl-1,4,6,9-tetrahydro-4,6-dioxopyrido[3,2-g]quinoline-2,8-dicarboxylate is prepared from the following types and amounts of ingredients:

| | |
|---|---|
| disodium 10-methyl-1,4,6,9-tetrahydro-4,6-dioxopyrido-[3,2-g]quinoline-2,8-dicarboxylate | 10 gm. |
| Dicalcium phosphate | 1,300 gm. |
| Methylcellulose, U.S.P. (15 cps.) | 60 gm. |
| Talc | 150 gm. |
| Corn starch | 200 gm. |
| Magnesium stearate | 12 gm. |

The compound and dicalcium phosphate are mixed well, granulated with 7.5 percent solution and methylcellulose in water, passed through a No. 8 screen and dried carefully. The dried granules are passed through a No. 12 screen, mixed thoroughly with the talc, starch and magnesium stearate, and compressed into tablets.

MAINTENANCE DOSE

A lot of 10,000 tablets, each containing 0.01 mg. of disodium 10-methyl-1,4,6,9-tetrahydro-4,6-dioxopyrido-[3,2g]quinoline-2,8-dicarboxylate is prepared from the following types and amounts of ingredients:

| | |
|---|---|
| disodium 10-methyl-1,4,6,9-tetrahydro-4,6-dioxopyrido-[3,2-g]quinoline-2,8-dicarboxylate | 0.1 gm. |
| Dicalcium phosphate | 1,500 gm. |
| Methylcellulose, U.S.P. (15 cps.) | 60 gm. |
| Talc | 150 gm. |
| Corn starch | 200 gm. |
| Magnesium stearate | 12 gm. |

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and magnesium stearate, and compressed into tablets.

These tablets are useful in preventing hay fever attacks at a dose of 1 priming dose tablet followed by one maintenance dose tablet every four hours.

EXAMPLE 2

PRIMING DOSE

One thousand two-piece hard gelatine capsules, each containing 1 mg. of disodium 10-methyl-1,4,6,9-tetrahydro-4,6-dioxopyrido[3,2-g]quinoline-2,8-dicarboxylate are prepared from the following types and amounts of ingredients:

| | |
|---|---|
| disodium 10-methyl-1,4,6,9-tetrahydro-4,6-dioxopyrido-[3,2-g]quinoline-2,8-dicarboxylate, micronized | 1 gm. |
| Talc | 180 gm. |
| Magnesium stearate | 2 gm. |

The ingredients are mixed well and filled into capsules of the proper size.

MAINTENANCE DOSE

One thousand two-piece hard gelatin capsules, each containing 0.1 mg. of disodium 10-methyl-1,4,6,9-tetrahydro4,6-dioxopyrido[3,2-g]quinoline-2,8-dicarboxylate are prepared from the following types and amounts of ingredients:

| | |
|---|---|
| disodium 10-methyl-1,4,6,9-tetrahydro-4,6-dioxopyrido- | |

| | |
|---|---|
| [3,2-g]quinoline-2,8-dicarboxylate, micronized | 0.1 gm. |
| Talc | 200 gm. |
| Magnesium stearate | 2 gm. |

The ingredients are mixed well and filled into capsules of the proper size.

Capsules so prepared are useful in preventing attacks of bronchial asthma at a dose of one priming dose capsule followed by one maintenance dose capsule every six hours.

EXAMPLE 3

PRIMING DOSE

A sterile preparation suitable for intramuscular injection and containing 1 mg. of di(tris-hydroxymethyl)-methylammonium 10-methyl-1,4,6,9-tetrahydro-4,6-dioxopyrido-[3,2-g]quinoline-2,8-dicarboxylate in each millimeter is prepared from the following ingredients:

| | |
|---|---|
| di(tris-hydroxymethyl)-methylammonium 10-methyl-1,4,6,9-tetrahydro-4,6-dioxopyrido[3,2-g]quinoline-2,8-dicarboxylate | 1 gm. |
| Benzyl benzoate | 200 ml. |
| Methylparaben | 1.5 gm. |
| Propylparaben | 0.5 gm. |
| Cottonseed oil q.s. | 1,000 ml. |

MAINTENANCE DOSE

A sterile preparation suitable for intramuscular injection and containing 0.02 mg. of di(tris-hydroxymethyl)-methylammonium 10-methyl-1,4,6,9-tetrahydro-4,6-dioxopyrido-[3,2-g]quinoline-2,8-dicarboxylate in each milliliter is prepared from the following ingredients:

| | |
|---|---|
| di(tris-hydroxymethyl)-methylammonium 10-methyl-1,4,6,9-tetrahydro-4,6-dioxopyrido[3,2-g]quinoline-2,8-dicarboxylate | 0.02 gm. |
| Benzyl benzoate | 200 ml. |
| Methylparaben | 1.5 gm. |
| Propylparaben | 0.5 gm. |
| Cottonseed oil q.s. | 1,000 ml. |

One milliliter of the priming dose is given followed by 1 ml. of maintenance dose every 4 to 12 hours for prophylactic treatment of allergic rhinitis.

EXAMPLE 4: Aqueous Solution 600 ml. of an aqueous solution containing 4 mg. of the di(tris-hydroxymethyl)methylammonium 10-methyl-1,4,6,9-tetrahydro-4,6-dioxopyride[3,2-g]quinoline-2,8-dicarboxylate per ml. is prepared as follows:

| | |
|---|---|
| di(tris-hydroxymethyl)-methylammonium 10-methyl-1,4,6,9-tetrahydro-4,6-dioxopyrido[3,2-g]quinoline-2,8-dicarboxylate | 2.4 gm. |
| Water for injection q.s. | 600 ml. |

The drug is dissolved in sufficient water to make 600 ml. and sterile filtered.

The solution is placed in nebulizers designed to deliver 0.25 ml. of solution per spray.

One dose of the solution is sprayed into the lungs initially and then the solution is diluted tenfold with sterile water and administered every four hours for prevention of asthmatic attacks.

EXAMPLE 5: Powder for Insufflation

PRIMING DOSE

A powder mixture consisting of 0.1 grams of di(trishydroxymethyl)methylammonium 10-methyl-1,4,6,9-tetrahydro-4,6-dioxopyrido[3,2-g]quinoline-2,8-dicarboxylate and sufficient lactose to make 5 grams of mixture is micropulverized and 50 mg. of powder placed in a capsule designed for placement in an insufflator to deliver 50 mg. of powder per dose.

MAINTENANCE DOSE

A powder mixture consisting of 10 milligrams of di(trishydroxymethyl)methylammonium 10-methyl-1,4,6,9-tetrahydro-4,6-dioxopyrido[3,2-g]quinoline-2,8-dicarboxylate and sufficient lactose to make 5 grams of mixture is micropulverized and 50 mg. of powder placed in a capsule designed for placement in an insufflator to deliver 50 mg. of powder per dose.

A priming dose capsule is taken first and then a maintenance dose capsule three times a day for prevention of asthmatic attacks.

EXAMPLE 6

Following the procedure of the preceding Examples 1 through 5, inclusive, compositions are similarly prepared substituting dimethyl 1,4,6,9-tetrahydro-10-methyl-4,6-dioxopyrido[3,2-g]quinoline-2,8-dicarboxylate, diethyl 1,4,6,9-tetrahydro-10-methyl-4,6-dioxopyrido[3,2-g]quinoline-2,8-dicarboxylate, disodium 1,4,6,9-tetrahydro-10-methyl 4,6-dioxopyrido[3,2-g]quinoline-2,8-dicarboxylate, di(tris-hydroxymethyl)-methylammoniumpyrido[3,2-g]quinoline-2,8-dicarboxylate, 10-chloro-1,4,6,9-tetrahydro-4,6-dioxo-5-(trifluoromethyl)-pyrido[3,2-g]quinoline-2,8-dicarboxylic acid, dimethyl 10-chloro-1,4,6,9-tetrahydro-4,6-dioxo-5-(trifluoromethyl)-pyrido[3,2-g]quinoline-2,8-dicarboxylate, 1,4,6,9-tetrahydro-4,6-dioxopyrido[3,2-g]quinoline-2,8,10-tricarboxylic acid, trimethyl 1,4,6,9-tetrahydro-4,6-dioxopyrido[3,2-g]quinoline-2,8,10-tricarboxylate, 10-chloro-1,4,6,9-tetrahydro-4-methyl-4,6-dioxopyrido[3,2-g]quinoline-2,8-dicarboxylic acid, dimethyl 10-chloro-1,4,6,9-tetrahydro-5-methyl-4,6-dioxopyrido[3,2-g]quinoline-2,8-dicarboxylate, 1,4,6,9-tetrahydro-10-methoxy-4,6-dioxopyrido[3,2-g]quinoline-2,8-dicarboxylic acid, dimethyl 1,4,6,9-tetrahydro-10-methoxy-4,6-dioxopyrido[3,2-g]quinoline-2,8-dicarboxylate, 10-fluoro-1,4,6,9-tetrahydro-4,6-dioxopyrido[3,2-g]quinoline-2,8-dicarboxylic acid, dimethyl 10-fluoro-1,4,6,9-tetrahydro-4,6-dioxopyrido[3,2-g]quinoline-2,8-dicarboxylate, 1,4,6,9-tetrahydro-3,7,10-trimethyl-4,6-dioxopyrido[3,2-g]quinoline-2,8-dicarboxylic acid, diethyl 1,4,6,9-tetrahydro-3,7,10-trimethyl-4,6-dioxopyrido[3,2-g]quinoline-2,8-dicarboxylate, 10-cyano-1,4,6,9-tetrahydro-4,6-dioxopyrido[3,2-g]quinoline-2,8-dicarboxylic acid, dimethyl 10-cyano-1,4,6,9-tetrahydro-4,6-dioxopyrido[3,2-g]quinoline-2,8-dicarboxylate, 5-methyl-1,4,6,9-tetrahydro-4,6-dioxopyrido[3,2-g]quinoline-2,8,10-tricarboxylic acid, trimethyl 1,4,6,9-tetrahydro-5-methyl-4,6-dioxopyrido[3,2-g]quinoline-2,8,10-tricarboxylate, 10-cyano-1,4,6,9-tetrahydro-5-methyl-4,6-dioxopyrido[3,2-g]quinoline-2,8-dicarboxylic acid, and dimethyl 10-cyano-1,4,6,9-tetrahydro-5-methyl-4,6-dioxopyrido[3,2- g]quinoline-2,8-dicarboxylate for the di(tris-hydroxymethyl)methylammonium 10-methyl-1,4,6,9-tetrahydro-4,6-dioxopyrido[3,2-g]quinoline-2,8-dicarboxylate or disodium 10-methyl-1,4,6,9-tetrahydro-4,6-dioxopyrido[3,2-g]quinoline-2,8-dicarboxylate of the examples.

I claim:

1. A process for treating asthma comprising the administration to a human of a priming dose of a pharmacologically acceptable salt or ester of a compound of the formula:

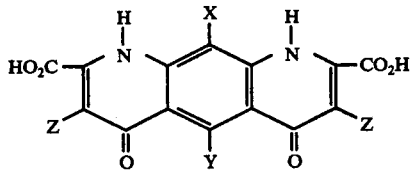

wherein X and Y can be the same or different and are selected from the group consisting of hydrogen, alkyl of from one to six carbon atoms, inclusive, cycloalkyl of five or six carbon atoms, inclusive, phenyl, hydroxyl, alkoxy having from one to three carbon atoms, inclusive, halogen, trifluoromethyl, cyano, carboxyamide and —$CO_2H$; Z is selected from the group consisting of hydrogen, alkyl from one to three carbon atoms, inclusive, and phenyl and provided when X is chloro at least one of Y and Z are other than hydrogen followed by the administration of a smaller maintenance dose consisting of 1/5th to 1/1000th the priming dose, said maintenance dose being repeated every 4 to 12 hours.

2. The process of claim 1 wherein the maintenance dose is 1/50th the priming dose.

3. The process of claim 1 wherein the compound is di(trishydroxymethyl)methylammonium 10-methyl-1,4,6,9-tetrahydro-4,6-dioxopyrido[3,2-g]quinoline-2,8-dicarboxylate.

4. The process of claim 1 wherein the compound is disodium 10-methyl-1,4,6,9-tetrahydro-4,6-dioxopyrido[3,2-g]quinoline-2,8-dicarboxylate.

* * * * *